(12) United States Patent
Woodmansee

(10) Patent No.: US 6,382,036 B1
(45) Date of Patent: May 7, 2002

(54) APPARATUS FOR MEASURING SURFACE PARTICULATE CONTAMINATION

(75) Inventor: Donald E. Woodmansee, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/670,452

(22) Filed: Sep. 26, 2000

(51) Int. Cl.⁷ .................................................. G01N 1/04
(52) U.S. Cl. .................................................... 73/864.71
(58) Field of Search ...................... 73/364.71; 15/143.1, 15/144.1, 209.1; 356/244, 237.2, 237.3

(56) References Cited

U.S. PATENT DOCUMENTS

| | | | | |
|---|---|---|---|---|
| 3,074,276 A | * | 1/1963 | Moos ........................ | 73/864.71 |
| 3,091,967 A | * | 6/1963 | Hurdlow et al. .......... | 73/864.71 |
| 5,373,748 A | * | 12/1994 | Lioy et al. ................ | 73/864.71 |
| 5,571,976 A | * | 11/1996 | Drolet ....................... | 73/864.71 |

* cited by examiner

Primary Examiner—Robert Raevis
(74) Attorney, Agent, or Firm—Pierce Atwood

(57) ABSTRACT

An apparatus for measuring surface particulate contamination includes a tool for collecting a contamination sample from a target surface, a mask having an opening of known area formed therein for defining the target surface, and a flexible connector connecting the tool to the mask. The tool includes a body portion having a large diameter section defining a surface and a small diameter section extending from the large diameter section. A particulate collector is removably mounted on the surface of the large diameter section for collecting the contaminants. The tool further includes a spindle extending from the small diameter section and a spool slidingly mounted on the spindle. A spring is disposed between the small diameter section and the spool for biasing the spool away from the small diameter section. An indicator is provided on the spindle so as to be revealed when the spool is pressed downward to compress the spring.

18 Claims, 1 Drawing Sheet

APPARATUS FOR MEASURING SURFACE PARTICULATE CONTAMINATION

STATEMENT REGARDING FEDERALLY SPONSORED RESEARCH & DEVELOPMENT

The U.S. Government may have certain rights in this invention pursuant to contract number DE-FC21-95-MC31176 awarded by the Department of Energy.

BACKGROUND OF THE INVENTION

This invention relates generally to cleanliness measurement and more particularly to a quantitative measurement of surface particulate contamination of mechanical system components.

Surface particulate contamination is a well-known source of mechanical system failures. This is particularly the case in power generating systems such as gas turbines where particulates can cause abrasion at the interface of moving parts, contaminate fluids flowing through the system, erode structures in high velocity fluid flow paths, and create deposits that either reduce desired flows or insulate against desired heat transfer. The provision of filters can control the flow of particulate contaminants into the system during operation. However, system components can become contaminated with particles during manufacture and assembly thereof. The presence of contaminants on components during assembly, which will not be captured by the filters, can result in the mechanical failures noted above.

A number of approaches to verify surface cleanliness of mechanical system components has been proposed. One such approach is the well known "white glove test" in which an inspector wipes a gloved finger across the surface of the component for some distance, and then observes the resultant stain on the finger. The inspector is then required to make an arbitrary decision as to the amount of contamination removed based on the darkness of the stain. This approach is highly subjective and varies greatly from test-to-test and from inspector-to-inspector. A more objective approach involves measuring particulate concentrations in the fluids used to wash the components. The fluid concentrations are typically determined using light attenuation or refraction, often with laser beams. However, this approach does not lend itself to practical, economic use on a mechanical assembly floor.

Another approach employs the use of "surface replicas." Here, the component surface to be sampled is covered with either an adhesive tape or a curable material that replicates the surface topography while also capturing loosely held surface particulate contamination. The surface is then scanned manually or with sophisticated optical recognition software to count particle numbers and sizes. This approach cannot give near instantaneous results on the factory floor and would be prohibitively expensive in most cases. Moreover, the sampled surface area is, by design, exactly equal to the size of the removed sample. Therefore, no amplification of the sampled area can be obtained.

Accordingly, there is a need for a quick, quantitative measurement of surface cleanliness for the factory floor assembly of mechanical system components.

BRIEF SUMMARY OF THE INVENTION

The above-mentioned need is met by the present invention which provides an apparatus for measuring surface particulate contamination that includes a tool for collecting a contamination sample from a target surface, a mask having an opening of known area formed therein for defining the target surface, and a flexible connector connecting the tool to the mask. The tool includes a body portion having a large diameter section defining a surface and a small diameter section extending from the large diameter section. A particulate collector is removably mounted on the surface of the large diameter section for collecting the contaminants. The tool further includes a spindle extending from the small diameter section and a spool slidingly mounted on the spindle. A spring is disposed between the small diameter section and the spool for biasing the spool away from the small diameter section. An indicator is provided on the spindle so as to be revealed when the spool is pressed downward to compress the spring.

The present invention and its advantages over the prior art will become apparent upon reading the following detailed description and the appended claims with reference to the accompanying drawings.

BRIEF DESCRIPTION OF THE DRAWINGS

The subject matter which is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

The present invention involves determining the cleanliness of a component surface by measuring the surface particulate contamination. This is accomplished by a procedure that is a quantification of the well-known "white glove" test often used by inspectors. In this procedure, a bright, white cloth swatch (referred to herein as a "smear") is first rubbed in a prescribed manner over a test surface, which is a known clean surface similar in surface roughness to the target surface on the component to be sampled. The purpose of rubbing a clean test surface is to precondition the smear for reflectivity loss that is solely attributable to abrasion effects. The roughened but still clean smear is then measured for its reflectivity using a reflectivity measuring instrument. Next, the smear is rubbed in a prescribed manner over the target surface to obtain a sample of the contamination on the target surface. The reflectivity of the smear is then measured again and compared to the first reflectivity measurement to determine the loss of reflectivity that is attributable to the contamination on the target surface. The loss of reflectivity is then related, through empirical calibration, to the amount of contamination that was transferred to the smear in the rubbing of the target surface. Thus, the procedure provides a quantified measurement of the surface contamination of the component that can be used as an objective "go/no go" indication for assembly. In other words, if the measured level of contamination is below a maximum acceptable level, then the component can go on to assembly. But if the measured contamination is above the acceptable level, then the component will need to be re-cleaned and re-checked prior to assembly.

Figure 1:
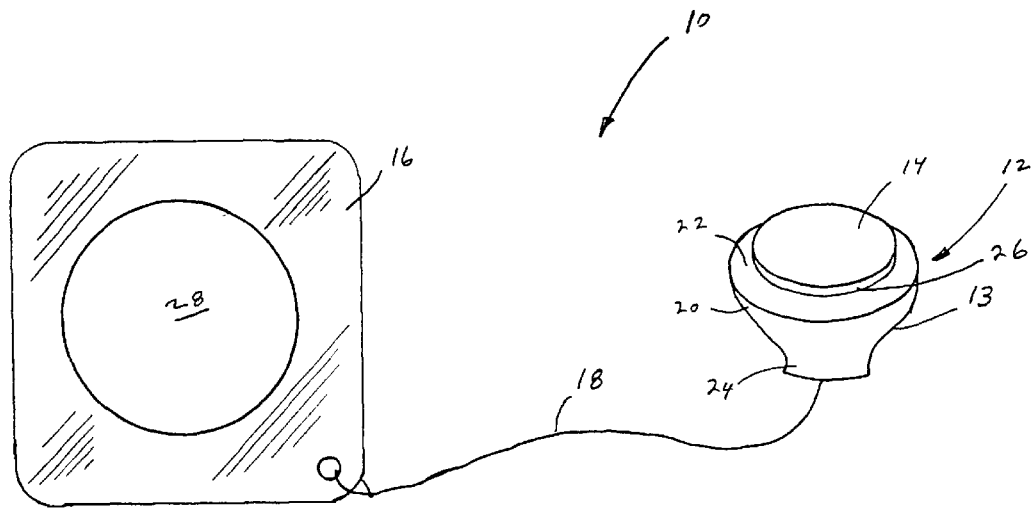
FIG. 1 shows an apparatus for collecting a contamination sample from a component surface for a cleanliness measurement.

Referring to the drawings wherein identical reference numerals denote the same elements throughout the various views, FIG. 1 shows an exemplary apparatus 10 for collecting the contamination sample. The apparatus 10 includes a hand tool 12 on which a particulate collector such as a white cloth smear 14 can be mounted and a mask 16 for delineating the area of the target surface to be sampled. The tool 12 and mask 16 are connected by a flexible connector 18 such as a string, cord or the like to insure that neither piece is inadvertently left behind after the measurement is completed.

The tool 12 includes a mushroom-shaped body portion 13 having a large diameter section 20 defining a spherically convex surface 22 and a small diameter section 24 extending from the large diameter section 20. In one preferred embodiment, the body portion 13 can comprise a commercially available knob of the type commonly used as a drawer pull or a handle for a cupboard door and typically made of wood, plastic, metal or the like. The smear 14 is mounted onto the spherically convex surface 22 so that the tool 12 can be used by grasping the small diameter section 24 and wiping the smear 14 over the target surface. The convex configuration of the smear 14 allows control of the leading interface of the smear 14 with the target surface during wiping. A thin layer 26 of a resilient material such as foam is interposed between the convex surface 22 and the smear 14. As used herein, a "resilient material" refers to materials that are compressible under the mentioned load and are also elastic. The foam layer 26, which can be approximately ⅛ inches thick, is fixedly secured to the convex surface 22 by any suitable means such as adhesive. The resilient foam 26 more uniformly distributes the pressure with which the tool 12 is applied to the target surface, thereby diffusing the load over a larger area so as to increase the contact area between the smear 14 and the target surface. The foam 26 is also elastic so as to retain its original shape after the compressive force is relieved.

The mask 16 comprises a thin sheet of a relatively stiff material that is thin enough (approximately 1/16 inch) to be somewhat flexible. One suitable material is a polytetrafluoroethlene polymer, such as that commercially available under the trademark TEFLON. An opening 28 of known area is formed in the mask 16 for limiting the area of the target surface that is to be sampled. The opening 28 is preferably, but not necessarily, circular in shape. The edge of the opening 28 is chamfered on the top side to prevent contamination from being caught therein. The mask 16 can be used on both flat surfaces and non-flat surfaces such as the interior of large pipes.

In one preferred embodiment, the smear 14 is a circular, white cloth swatch sized to fit onto the convex surface 22. One suitable smear is commercially available from D. A. Services, Inc. of Windsor, Conn. These smears are bright white cloth disks 1¾ inches in diameter and come stored in a waxed paper folder that can be labeled for archiving. The smears also have a multi-use contact adhesive backing (not shown in FIG. 1) that allows them to be removably mounted on the foam layer 26. When using the 1¾ inch smears from D. A. Services, Inc., the large diameter section of the hand tool 12 preferably has a 2 inch diameter and the mask opening 28 is preferably a 6 inch diameter circle.

One preferred procedure for determining the cleanliness of a component surface will now be described in greater detail. The first step is to select a new smear for the measurement and measure its reflectivity to simply verify that the smear is new and unused. This is done by opening the smear folder and measuring the smear reflectivity once or twice with a reflectivity measuring instrument. The actual reflectivity value is recorded. Any suitable instrument can be used for this purpose. One suitable commercially available device is the Photovolt Model 577 from UMM Electronics of Ind., Indiana. This device includes a reflectivity meter and sensor set up to operate with a blue filter where the smear is pressed against the face of the sensor head. The sensor head has a ¾ inch hole in its distal end and contains both a light source and a photomultiplier, which illuminate and measure reflectance from objects placed against the hole.

The next step is to remove the smear 14 from its paper folder and place it in position on the convex surface 22 of the tool 12. This is preferably done using tweezers so as to avoid contaminating the smear 14 prior to the measurement. Once properly placed on the tool 12, the smear 14 is wiped in a prescribed manner over a test surface to precondition the smear 14 for reflectivity loss that is solely attributable to abrasion effects. As mentioned above, the test surface is a known clean surface similar in surface roughness to the target surface to be sampled. One preferred test surface is a small portion of the component surface being measured that has been sufficiently cleaned so that all contamination is known to have been removed. Specifically, if the component surface has been subjected to oil removal processes, the test surface should be a non-sampled section of the surface that has been wiped clean using an alcohol-based cleaner and a laboratory paper towel. If the component surface has been cleaned but not subjected to oil removal processes, the test surface should be a non-sampled section of the component surface that has been wiped clean twice with a clean, dry cotton rag, wiping hard (approximately 2 lbf).

After the preconditioning wipe is completed, the smear 14 is transferred back to its folder, again using tweezers. The reflectivity of the roughened but still clean smear is then measured using the reflectivity measuring instrument while the smear 14 is mounted in its folder. Typically, a 5-point measurement of reflectivity is obtained, taking the measurements ¼ inch off the smear center in each direction, with each measurement representing a substantially different area of the smear 14. The results of the five measurements are then averaged to obtain a single reflectivity value for the smear 145. All of the measurements are recorded on the folder. The smear 14 is then removed from the folder again and remounted on the tool 12 for a target surface sampling wipe.

The mask 16 is placed on the component surface so as to defme the target surface within the mask opening 28. This forces the sampling wipe to be conducted on a controlled region of known area. The smear 14 is wiped over the target surface in a prescribed manner to obtain a sample of the contamination on the component surface. The preconditioning wipe and the sampling wipe are preferably conducted in identical manners. In one preferred wiping procedure, the smear 14 is wiped over the target surface in a spiral motion, starting at the center of the masked opening 28 and moving outward to the edge of the opening 28 in gradually increasing circles. The tool 12 is held with its axis tilted so that the forward edge of the smear 14 is lifted as it passes over the target surface. Furthermore, as the smear 14 is moved, it is rotated into the direction of motion so as to continually provide a fresh surface of the smear 14 to pick up contamination. As the wiping path approaches the chamfered edge of the mask opening 28, the tool 12 is further tilted so that the smear 14 rides up slightly over the mask 16 while the wiping motion is tangential to the edge. This overlap enables any contaminates that have been inadvertently rubbed onto the mask to be captured. Furthermore, the tangential motion minimizes the tendency to rub contamination from the target area out under the mask 16. Generally, each pass should be done with a relatively constant force and in a prescribed time period such as 5 seconds.

Two such spiral passes of the target surface are usually sufficient to capture all the surface contamination on the smear 14. Thus, a single wiping procedure will comprise two passes. The second pass not only collects residue contamination missed in the first pass, but will also further smudge the contamination around the smear 14 to provide a more uniform darkening thereof. Using more than two passes in a single wipe would only tend to have an adverse effect on the reflectivity measurement. For example, additional passes would tend to push the contamination from the surface of the smear 14 into its interior and degrade the smear surface with excessive abrasion. These confounding effects on the ultimate reflectivity measurement can be avoided by following the prescribed procedure each time. Accuracy, repeatability and reproducibility of the measurements depend on conducting the sampling procedure consistently every time the measurement is conducted.

Next, the smear 14 is removed from the tool 12 and returned to its folder with tweezers. The smear reflectivity after sampling is measured using the reflectivity measuring instrument as described above. The reflectivity measurement is preferably made a short time after the sampling, although it can be made at any time since the smear reflectivity value is not a sensitive function of aging. The reflectivity measurements, date and time of sampling, technician, component and target surface area (as defined by the mask opening 28) are recorded on the folder. The amount of contamination collected from the target surface is determined by calculating the change in reflectivity of the smear as measured before and after the sampling and comparing that to a previous calibration using a similar contamination. As mentioned above, if the measured level of contamination is below a maximum acceptable level, then the component can go on to assembly. But if the measured contamination is above the acceptable level, then the component will need to be re-cleaned and re-checked prior to assembly.

The smear 14 can be stored in its folder for later examination and comparisons. If the need arises, the smear 14 can be submitted for metals analysis by scanning electron microprobe. Moreover, wet chemical analyses can be done at a later time if desired to determine the exact chemical composition and contaminant loading. An unused smear should be retained with the archived smears on a regular basis (such as once per week or one per a 500 smear box). These unused smears serve as controls for later re-measurements of smear reflectivity or of contaminant concentrations.

The calibration for determining the amount of contamination collected on the smear 14 can be performed as follows. A sample of representative contaminant material is collected from component surfaces or special specimens located in the assembly areas that contribute contamination. This sample contaminant material is carefully placed on a weigh paper and weighed in a laboratory balance to obtain the gross weight. A mask 16 is placed on a calibration surface, and the sample is distributed on the calibration target surface within the mask opening 28. Preferably, the calibration surface is a flat plate of a material having the same roughness as the component surface to be sampled. The empty weigh paper is then re-weighed to obtain the tare weight such that the net weight of the sample material can be determined. Then a sample wiping procedure is performed in the manner described above using a clean smear 14, and reflectivity measurements of the smear 14 are taken before and after the sampling to determine the loss of reflectivity. Results are graphed as the loss in reflectivity of the smear as a function of the mass of sample material placed inside the calibration target area. Thus, the calibration is able to correlate a measured loss in reflectivity to a quantified mass of contamination.

Various enhancements to the above described procedure are also possible. For example, it may be beneficial to pre-coat the smear 14 with a clear, somewhat tacky coating to enable it to collect and hold large amounts of loose particles. Such a coating can be applied before the first pass of a sampling wipe, before the second pass of a sampling wipe, or before both passes. It may also be useful to spray the target surface with a clear liquid cleaner to help release contamination from the target surface and facilitate transfer to the smear 14. Moreover, the presence of any remnant oil films on the target surface may dictate that the calibration surface be provided with the same level of oil film, since the oil (even without particles) will likely reduce the smear reflectivity. Alternatively, the presence of oil films could be dealt with by soaking the smear for a long time to vaporize the organics, leaving only the particulate contamination to affect the smear reflectivity.

Figures 2, 3:
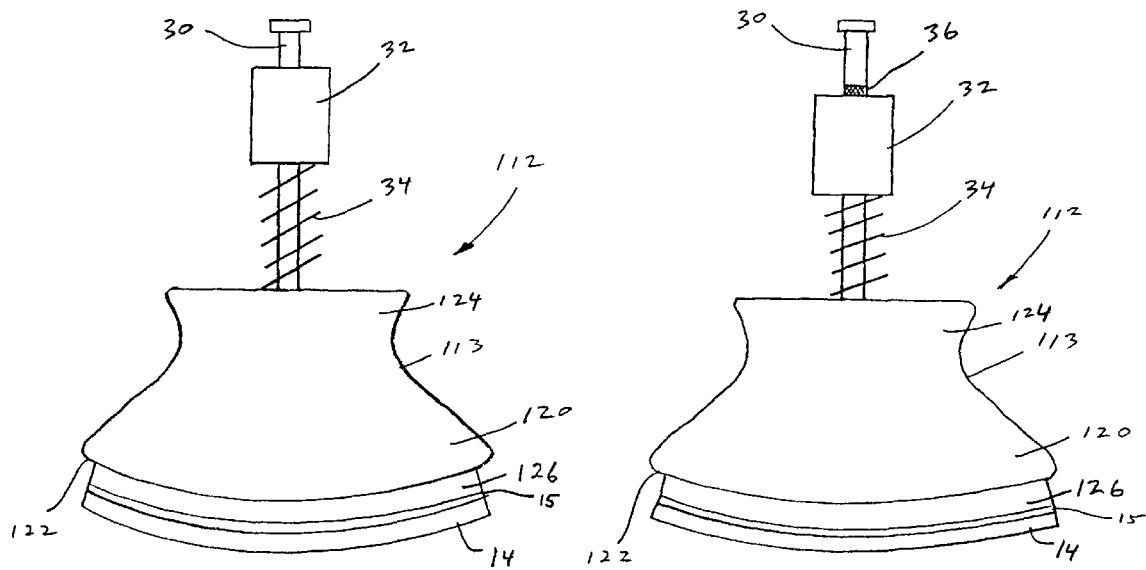
FIGS. 2 and 3 show an alternative embodiment of a hand tool that can be used in the apparatus of FIG. 1.

Referring now to FIGS. 2 and 3, an alternative embodiment of a hand tool 112 is shown. As in the first embodiment, the tool 112 includes a mushroom-shaped body portion 113 having a large diameter section 120 defining a spherically convex surface 122 and a small diameter section 124 extending from the large diameter section 120. A smear 14 is mounted onto the spherically convex surface 122 with a thin layer 126 of a resilient material such as foam interposed between the convex surface 122 and the smear 14. The smear 14 includes a multi-use contact adhesive backing 15 for repeated and removable mounting to the foam layer 26.

In this embodiment, a spindle 30 extends axially from the end of the small diameter section 124. A spool 32 having a bore formed therein along its longitudinal axis is slidingly mounted on the spindle 30, and a spring 34 is disposed between the end of the small diameter section 124 and the spool 32 for biasing the spool 32 away from the small diameter section 124. A color band 36 or a similar indicator is formed on the spindle 30 at a location such that it is covered by the spool 32 when the spool 32 is in its normal position such that the spring 34 is in an uncompressed state (FIG. 2). Pressing the spool 32 downward along the spindle 30 to expose the color band 36 (FIG. 3) will cause the spring 34 to be compressed. Thus, when performing a wiping procedure, be it a preconditioning wipe, a sampling wipe or a calibration wipe, the operator will hold the sliding spool 32 and press it downward to expose the color band 36. This will allow the operator to press the tool and smear 14 against the surface with a known amount of force (about 170–210 g), so as to insure uniform application of the tool 112 each procedure.

The foregoing has described a method and apparatus for measuring surface particulate contamination. The present invention has several benefits for use on the factory floor. For example, because the stain on the smear is very visible to the operator, the technique is intuitive and readily understood by the technician, even without technical training. The reflectivity measurement can be made on the factory floor within minutes of the smear being wiped on the target surface. This is very helpful in getting broad acceptance of the technique given the time pressures of a major manufacturing and assembly operation. The ability of the technician to conduct both the sampling and the reflectivity measurements improves the likelihood that the process will be consistently used, thereby continually reinforcing the need to work cleanly. Because the area of the target surface is larger then the smear (almost 12 times larger in the exemplary embodiment described above), the sample improvement will realize an order of magnitude improvement over using replicas, even if the smear collection was only 90% effective. Another advantage is that the smears can be easily archived in their folders for later re-measurement of reflectivity or for physical and/or chemical analysis of the contaminant material.

While specific embodiments of the present invention have been described, it will be apparent to those skilled in the art that various modifications thereto can be made without departing from the spirit and scope of the invention as defined in the appended claims.

What is claimed is:

1. An apparatus for measuring surface particulate contamination comprising:

a tool having a body portion, wherein said body portion includes a large diameter section defining a spherically convex surface, and a small diameter section extending from said large diameter section, and a particulate collector removably attached to said surface of said large diameter section;

a mask having an opening of known area formed therein; and a flexible connector connecting said tool to said mask.

2. The apparatus of claim 1 further comprising:

a spindle extending from said small diameter section, said spindle having an indicator formed thereon;

a spool slidingly mounted on said spindle; and a spring disposed between said small diameter section and said spool for biasing said spool away from said small diameter section, wherein said indicator is covered by said spool when said spring is in an uncompressed state and said indicator is not covered by said spool when said spring is in compressed by said spool.

3. The apparatus of claim 1 wherein said particulate collector comprises a white cloth smear.

4. The apparatus of claim 3 wherein said smear has a multi-use contact adhesive backing formed on one side thereof.

5. The apparatus of claim 3 further comprising a layer of a resilient material interposed between said surface of said large diameter section and said smear.

6. The apparatus of claim 5 wherein said resilient material is a foam.

7. An apparatus for measuring surface particulate contamination comprising:

a tool having:
      a body portion having a large diameter section defining a surface and a small diameter section extending from said large diameter section;
      a particulate collector removably mounted on said surface of said large diameter section;
      a spindle extending from said small diameter section, said spindle having an indicator formed thereon;
      a spool slidingly mounted on said spindle; and
      a spring disposed between said small diameter section and said spool for biasing said spool away from said small diameter section, wherein said indicator is covered by said spool when said spring is in an uncompressed state and said indicator is not covered by said spool when said spring is in compressed by said spool;

a mask having an opening of known area formed therein; and a flexible connector connecting said tool to said mask.

8. The apparatus of claim 7 wherein said particulate collector comprises a white cloth smear.

9. The apparatus of claim 8 wherein said smear has a multi-use contact adhesive backing formed on one side thereof.

10. The apparatus of claim 8 further comprising a layer of a resilient material interposed between said surface of said large diameter section and said smear.

11. The apparatus of claim 10 wherein said resilient material is a foam.

12. The apparatus of claim 7 wherein said surface of said large diameter section is spherically convex.

13. A tool for collecting a contamination sample from a target surface, said tool comprising:

a body portion having a large diameter section defining a surface and a small diameter section extending from said large diameter section;

a particulate collector removably mounted on said surface of said large diameter section;

a spindle extending from said small diameter section, said spindle having an indicator formed thereon;

a spool slidingly mounted on said spindle; and a spring disposed between said small diameter section and said spool for biasing said spool away from said small diameter section, wherein said indicator is covered by said spool when said spring is in an uncompressed state and said indicator is not covered by said spool when said spring is in compressed by said spool.

14. The tool of claim 13 wherein said particulate collector comprises a white cloth smear.

15. The tool of claim 14 wherein said smear has a multi-use contact adhesive backing formed on one side thereof.

16. The tool of claim 14 further comprising a layer of a resilient material interposed between said surface of said large diameter section and said smear.

17. The tool of claim 16 wherein said resilient material is a foam.

18. The tool of claim 13 wherein said surface of said large diameter section is spherically convex.

* * * * *